United States Patent [19]

Boomgaarden et al.

[11] Patent Number: 5,433,222
[45] Date of Patent: Jul. 18, 1995

[54] BODY RESTRAINT DEVICE

[75] Inventors: Jonathan C. Boomgaarden, Waukesha; William O. Schoenbeck, Oconomowoc, both of Wis.

[73] Assignee: General Electric Company, Milwaukee, Wis.

[21] Appl. No.: 237,218

[22] Filed: May 3, 1994

[51] Int. Cl.$^6$ .......................... A61B 19/00; A44B 1/04
[52] U.S. Cl. ...................... 128/869; 24/72.5; 128/876
[58] Field of Search ............... 128/869, 874, 875, 876; 24/72.5, 462; 5/658, 503.1, 424

[56] References Cited

U.S. PATENT DOCUMENTS

| | | | |
|---|---|---|---|
| 2,043,555 | 6/1936 | Preston | 24/72.5 |
| 2,784,423 | 3/1957 | Droeger | 5/503.1 |
| 3,313,511 | 4/1967 | Koerner | 5/424 |
| 3,337,880 | 8/1967 | Florek | 5/503.1 |
| 3,398,919 | 8/1968 | Toker | 5/503.1 |
| 4,487,523 | 12/1984 | Monroe | 5/658 |
| 4,729,138 | 3/1988 | Heyman | 5/424 |
| 4,998,277 | 3/1991 | Rioux | 5/503.1 |

Primary Examiner—Michael A. Brown
Attorney, Agent, or Firm—James J. Lichiello; John H. Pilarski

[57] ABSTRACT

A strap latch device for securing a medical patient to the side rails of an examining or treatment table includes a pair of extending opposed claw arms, one fixed and the other spring biased to rotate towards the fixed claw arm with the arms overlying a rectangular recess in the latch between the arms. A lever is used to overcome the bias and separate the claw arms so that one edge of a side rail fits into the fixed claw arm and rotation of the latch on the rail projects to the moveable claw arm over the side rail with the side rail fitting closely into the defined recess. Upon release of the bias lever the side rail is grasped by the claw arms with projecting lips on the claw arms securing the rail into its recess. Patient motion and belt tension will tend to accentuate latch retention.

8 Claims, 2 Drawing Sheets

BODY RESTRAINT DEVICE

BACKGROUND OF THE INVENTION

This invention relates to a body restraint device and more particularly to a human body restraint for medical patient treatment purposes, Some medical treatments require that the patient be restrained from moving from a predetermined position during the treatment procedures, For example, in certain cardiac applications the patient may be in an upright position and unconscious so that any body movement may not be fully controllable by the patient, Such a patient may be fastened to a tilting table which is tilted into an upright patient position, In such an instance, a knee flexure, for example, voluntary or involuntary, may deleteriously alter a precision position of the patient under treatment. For applications of the kind described, a knee restraint is desired, particularly one which attaches to the existing side rail of current EP (electrophysiology) tables. These side rails generally comprise a rectangular cross-section bar passing longitudinally along the sides of a long rectangular table on which a patient rests. Such a restraint preferably occupies a minimal length of side rail and must be easily and quickly attached to and released from a side rail with a required positive attachment which will not accidentally release or loosen.

Accordingly, it is an object of this invention to provide an improved patient restraint device having a positive attachment and positive release arrangement wherein any patient motion serves to reinforce positive engagement.

SUMMARY OF THE INVENTION

A strap latch means for patient restraint purposes includes a strap attached latch having extended, opposed claw arms to oppositely grip a rectangular side rail of an EP (electrophysiology) table, One claw arm of the latch is fixed while the opposite claw arm is adapted for some rotation to remove its claw from the side rail. Release of the latch requires a positive and intentional manipulation to release the moveable claw and rotate the latch. Disengaging rotation is prevented by any involuntary motion of the restrained patient since the resulting belt tension accentuates locking rotation of the latch.

This invention will be better understood when taken in connection with the following drawing and description.

BRIEF DESCRIPTION OF A PREFERRED EMBODIMENT

Figure 1:
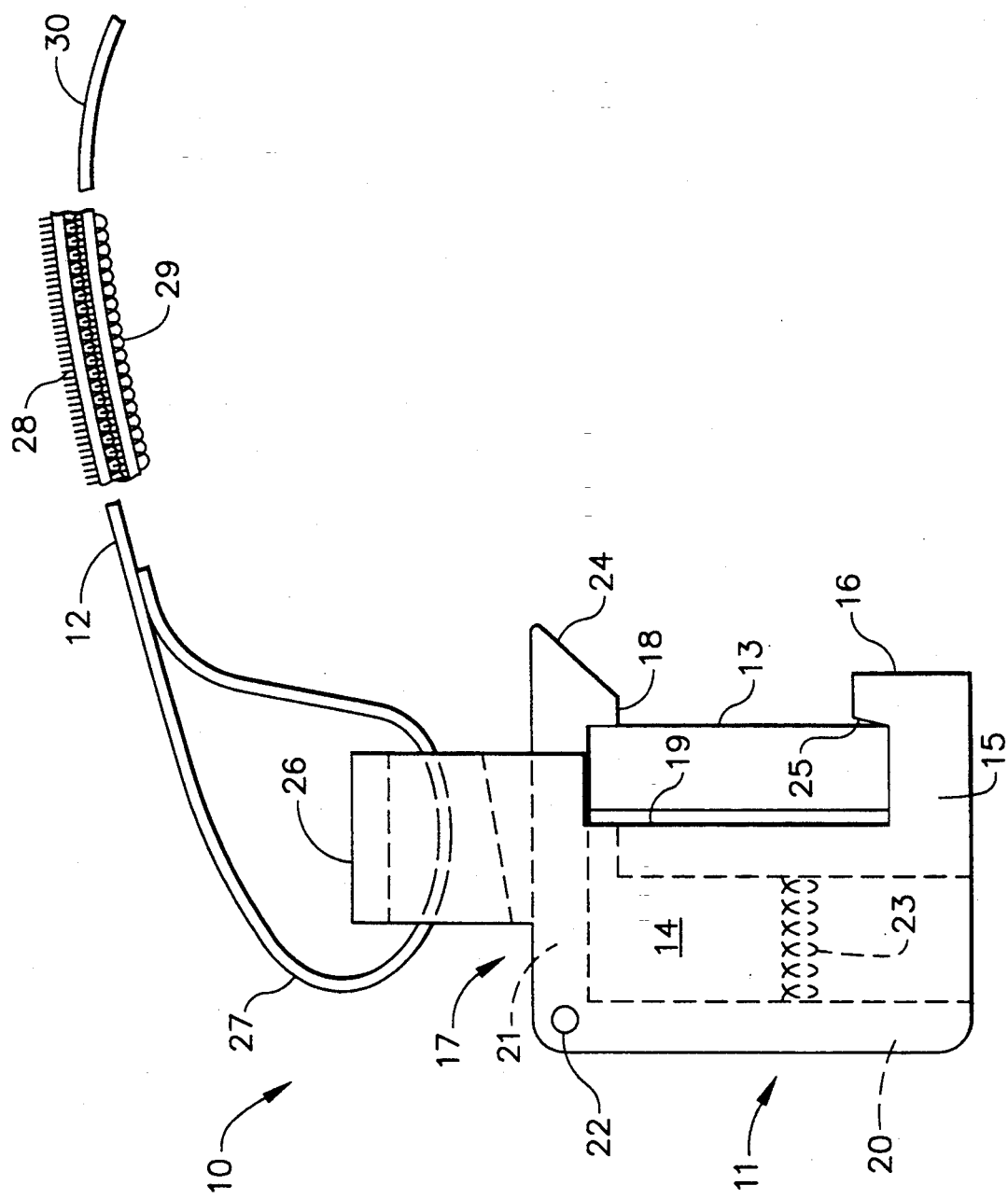
FIG. 1 is a schematic and cross-sectional illustration of the strap latch positive patient restraint means of this invention in its locked or engaged position.

Referring now to FIG. 1, a patient restraint assembly 10 comprises a locking latch 11 attached to a belt or strap 12 and to a table side rail 13. Belt 12 passes over a patient's body or appendage to engage an opposite rail with a similar latch 11 and belt 12, Latch 11 comprises a frame body 14 formed with an integral lower claw arm 15 extending therefrom and terminating with an upturned lip 16 which surrounds a lower edge of rail 13, An upper and opposite claw arm 17 is fitted to and extends from frame 14 and terminates in a downturned lip 18, Lips 16 and 18 project at right angles towards each other to partially surround the opposite edges of rail 13 to effectively secure rail 13 therebetween with the lips 16 and 18 also preventing any relative lateral motion between frame 14 and rail 13. Additionally, frame 14 includes a rectangular recess 19 which serves to more closely secure rail 13 therein for improved latching purposes as illustrated in FIG. 1 where claw lips 16 and 18 fully engage rail 13 so that frame 14 and its belt 12 are firmly mechanically locked to rail 13.

In order to initially latch frame 14 to rail 13 and to rapidly and easily disengage frame 14 from rail 13, upper claw arm 17 is formed as an angular lever arm comprising a recessed operating lever arm 20 and a claw arm 21. Claw arm 17 is adapted to have its lip 18 moveable towards and away from lip 16 of arm 15. Preferably this movement is of a rotary nature and is provided by having claw arm 17 pivotally attached to frame 14 with pivot pin 22 which permits claw arm 17 to rotate in a plane parallel to frame 14 and perpendicular to rail 13. Disengagement and reengagement of latch 11 to rail 13 is best described with respect to FIG. 2.

Figure 2:
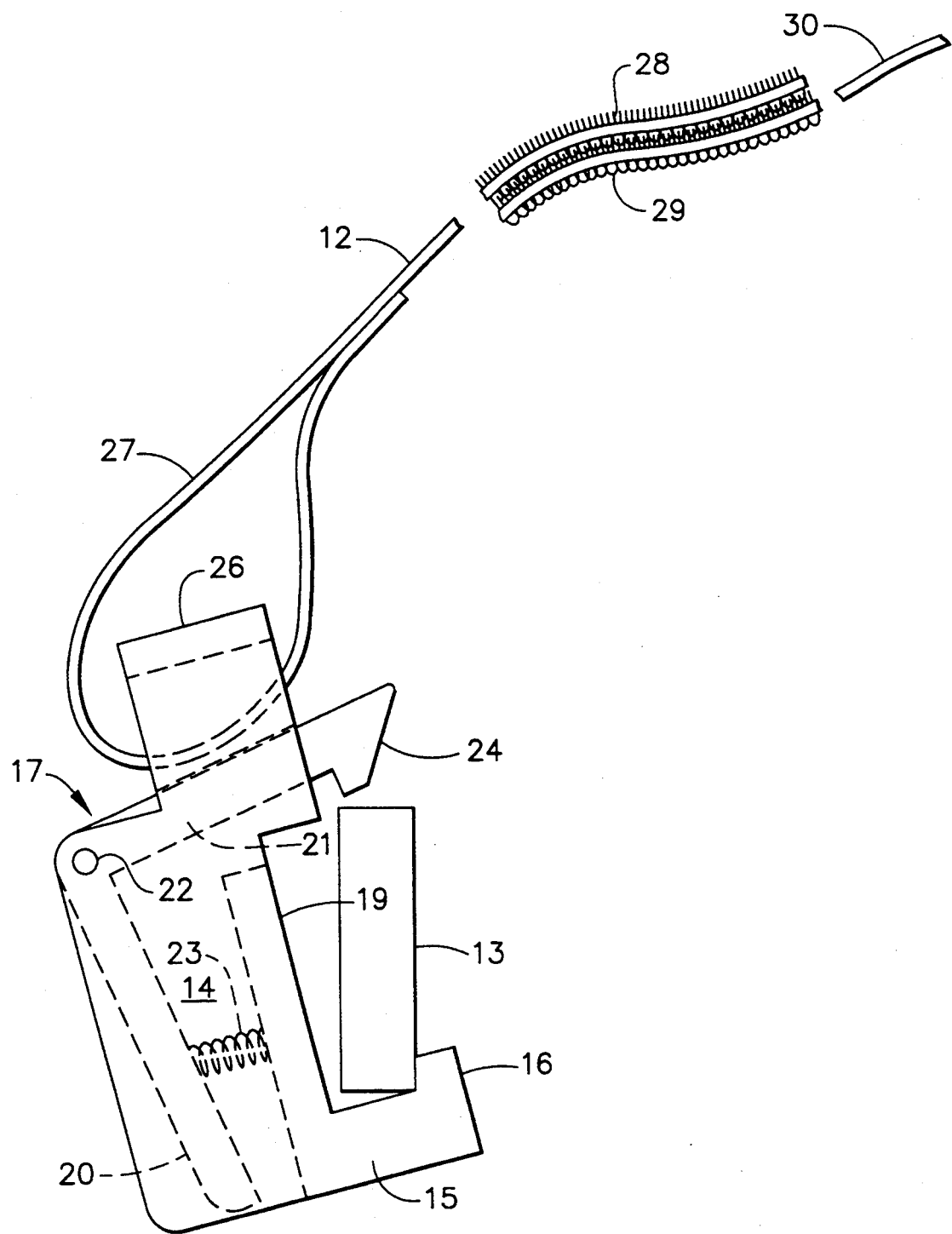
FIG. 2 is a schematic and cross-sectional illustration of the strap latch positive patient restraint means of FIG. 1 during its disengaging action.

Referring now to FIG. 2, disengagement of frame 14 is accomplished by depressing operating arm 20 against the biasing action of spring means 23 between an appropriate part of frame 14 and operating arm 20 so that claw arm 17 and lip 18 are moved up and away from rail 13. Thereafter, frame 14 may be rotated in a counter-clockwise direction as illustrated in FIG. 2 and, because of the vertical clearance obtained by this separating action between claw arm 17 and rail 13, frame 14 may also be moved downwardly and away from rail 13. To engage frame 14 to rail 13, operating arm 20 is depressed against spring 23 to increase the separation between lips 16 and 18. Arms 15 and 21 are then caused to partly encircle rail 13 so that one edge of rail 13 fits in arm 15 adjacent lip 16 as illustrated in FIG. 2. Frame 14 is then rotated clockwise to bring lip 18 fully over rail 13 and operating arm 20 is released so that spring 23 causes claw arm 17 to rotate clockwise and lip 16 mechanically grips rail 13 as illustrated in FIG. 1. If arm 20 is inadvertently not sufficiently depressed to provide sufficient separation of lips 16 and 18, the tapered surface 24 of lip 18 will bear against rail 13 to provide a camming action to further move lip 18 over rail 13. For low wear characteristics arms 15 and 17 and lips 16 and 18 are preferably metallic. Proper dimensioning of the latch will permit easy attachment by merely hooking lower lip 16 around rail 13 as described and rotating frame 14 clockwise so that the described camming action is sufficient to move lip 18 over rail 13. Lever arm 20 of claw arm 17 is recessed in frame 14 as an additional safety factor against inadvertent or accidental depression.

Flexible belt or strap 12 is appropriately attached to frame 14 by means of a loop extension 26 of frame 14 interconnecting with a loop 27 of strap 12. In a usual strap restraint system, straps are connected to opposite side rails of an EP table and extend oppositely across a patient, and are suitably joined together by various joining means. In this invention, and as illustrated in FIG. 1, a pair of opposite straps will be conveniently similar, for example, with Velcro hooks 28 on the upper or outer surface of a belt 12 with respect to the patient on the table and Velcro loops 29 on the inner surface and similarly for the opposite strap 30 and its latch (not shown). By this means, either strap may be placed first across the patient and the other strap secured to it and over it. When opposite straps are secured to each other for the desired restraint any tension in the straps, voluntary or involuntary by the patient serves to keep the latch engaged, and any relaxation of strap tension does not loosen the latch because of the spring biasing of the lever arm 17. Recess 19 and arms 15 and 17 together with their lips 16 and 18 are proportioned to permit the latch of this invention to slide along rail 13.

This invention provides a patient restraint strap latch device to engage the side rails of an EP table, and which requires only a small length of the side rail. Personal safely of patient restraint means is extremely important and the strap latch device of the present invention is inherently safe, As previously described, only a modest tension in the secured belt across the patient serves to accentuate the rail attachment and prevent the rotation of frame 14 necessary to release the latch. Accordingly, when the restraint device is employed, for example, across the thighs or shins of an upright patient on an EP table, any knee flexure will only serve to retain the latched condition of the restraint and the patient position.

While this invention has been disclosed and described with respect to one preferred embodiment, it will be understood by those skilled in the art that various changes and modifications may be carried out without departing from the spirit and scope of this invention.

What is claimed:

1. An opposed claw latching device adapted for connection to a flexible strap of a patient restraint system, and to a rectangular cross-section rail comprising in combination,
   (a) a latch frame,
   (b) a pair of opposed upper and lower claw arms extending from said frame each with a projecting lip at the end thereof projecting towards each other,
   (c) one of said claw arms being fixed to said frame,
   (d) the other of said claw arms being movably attached to said frame for motion towards and away from said fixed claw arm,
   (e) biasing means biasing said moveable claw arm towards said fixed claw arm,
   (f) said frame having a recess adapted to receive said rail therein,
   (g) said claw arms defining upper and lower edges of said recess with said lips overhanging said recess,
   (h) means to move said moveable claw arm against said biasing means to move its lip away from said recess so that said fixed claw arm may receive an edge of said rail in said recess and adjacent said lip on said fixed claw arm so that concurrent rotation of said frame towards said rail fully fits said rail in said recess to be retained therein by said opposed lips,
   (i) and flexible strap means attached to said frame.

2. The invention as recited in claim 1 wherein said lip on said upper claw arm includes a tapered camming surface to bear against said rail so that said concurrent rotation will produce a camming force on said pivotable claw arm to necessarily move it an additional distance from said recess to permit entry of said rail into said recess.

3. The invention as recited in claim 1 wherein said lip on said fixed claw arm includes a tapered surface next adjacent said rail in said recess and tapering away from said rail to facilitate rail entry into said recess.

4. The invention as recited in claim 1 wherein said moveable claw arm is pivoted to said frame for rotary motion towards said fixed claw arm.

5. The invention as recited in claim 1 wherein said lips and said recess include dimensions which permit said latch to slide longitudinally along said rail.

6. The invention as recited in claim 1 comprising a pair of latch devices and a flexible strap attached to each device.

7. The invention as recited in claim 6 wherein each of said flexible straps includes attachment means adjacent an end thereof for attachment to a further flexible strap.

8. The invention as recited in claim 7 wherein said attachment means is provided on each of said straps and comprises myriads of Velcro hooks on one side of said strap and myriads of Velcro loops on the opposite side.

* * * * *